(12) United States Patent
Dudee

(10) Patent No.: US 7,819,528 B1
(45) Date of Patent: Oct. 26, 2010

(54) TABLE-FREE MOUNTING SYSTEM FOR SLIT LAMP BIOMICROSCOPE ASSEMBLY

(76) Inventor: Jitander Singh Dudee, 2459 Nicholasville Rd., Lexington, KY (US) 40503

( * ) Notice: Subject to any disclaimer, the term of this patent is extended or adjusted under 35 U.S.C. 154(b) by 0 days.

(21) Appl. No.: 12/493,531

(22) Filed: Jun. 29, 2009

(51) Int. Cl.
*A61B 3/00* (2006.01)
*A61B 3/10* (2006.01)

(52) U.S. Cl. ..................... 351/245; 351/214
(58) Field of Classification Search .......... 351/200–246
See application file for complete search history.

(56) References Cited

U.S. PATENT DOCUMENTS

| | | | |
|---|---|---|---|
| 3,652,153 A * | 3/1972 | Gambs | 351/214 |
| 5,216,456 A * | 6/1993 | Volk | 351/214 |
| 5,424,789 A * | 6/1995 | Volk | 351/216 |
| 6,283,596 B1 * | 9/2001 | Yoshimura et al. | 351/214 |
| 7,670,003 B2 * | 3/2010 | Kendrick | 351/214 |

* cited by examiner

*Primary Examiner*—Mohammed Hasan

(57) ABSTRACT

An apparatus providing a means for slit lamp biomicroscopes and similar opthalmological instruments to be accurately positioned and controlled without the need for a table base under the instrument, comprising an overhead assembly and mounting device which allows controlled movement and positioning of the slit lamp and associated illumination system in all three spatial axes. The overhead location of the support and movement mechanism combined with a joystick control on the instrument arm eliminates ergonomic obstacles allowing the instrument to be used when examining patients in wheelchairs and those affected by medical and anatomic restrictions.

2 Claims, 4 Drawing Sheets

TABLE-FREE MOUNTING SYSTEM FOR SLIT LAMP BIOMICROSCOPE ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Field of Search: 351/200,211-221,206,245,246

The slit lamp biomicroscope is widely considered an essential diagnostic instrument in the field of opthalmology and consists of two principal components: a bright focal source of light projecting an illuminating beam whose cross section forms a slit of variable width or height; and a microscope, usually binocular to view the area of interest illuminated directly or indirectly by the slit beam.

The corneal binocular microscope component was the first to be developed and has been attributed to Aubert in 1891 who enhanced Louis de Wecker's monocular microscope invention. Siegfried Czapski's refined this instrument into a corneal surface microscope with stand, developed by Zeiss in 1899. The first instrument to feature slit illumination appears to have been that developed by Allvar Gullstrand (1862-1930) and demonstrated at Heidelberg in 1911.

Henker and Vogt improved upon Gullstrand's device in the 1910s by creating an adjustable slit lamp and combining Czapski's microscope with Gullstrand's slit lamp illumination to develop the Zeiss Slit lamp in 1916. This resulted in a binocular microscope coupled, around the same axis, with a bright light source allowing different illuminations and magnified views of the eye.

In 1933, Hans Goldmann (1899-1991) working under Professor Siegrist of Bern, devised a joystick controlled mechanism to focus the illumination system and the corneal microscope components together in a coordinated manner.

The slit lamp biomicroscope was thus established as an essential diagnostic tool by the Opthalmology community and subsequently enhanced and adapted to allow additional diagnostic and therapeutic functions including digital imaging and laser delivery.

Varieties of tables for supporting a slit lamp microscope and associated ophthalmic instruments have been developed over the years and are known in the art. In the prior art, a slit lamp assembly generally included a base set upon a table with means to adjust the table height and position to accommodate the particular individual whose eyes were being examined.

Ophthalmic examination takes place by use of the slit lamp biomicroscope which normally sits upon the top side of the table. When being examined, the patient must place his or her chin on a chin rest and must rest his or her forehead on a forehead support both supporting structures being attached to the slit lamp table. The proper placement of a patient's chin and forehead is essential to ensure the patient's head and eyes remain in a steady position in relation to the slit lamp biomicroscope. In addition a movable slit illumination system is necessary whose vertical axis of rotation is fixed in relation to the focal point of the binocular lens eyepiece system of the slit lamp biomicroscope so that the details of the eye can be both properly illuminated and viewed.

The prior art slit lamp biomicroscope assembly includes a table, generally rectangular in shape, located underneath the slit lamp biomicroscope. The table requires certain minimum dimensions to allow translation (controlled movement), support, placement and fixation of the slit lamp biomicroscope in order to perform examination and treatment of the eyes being studied. The table base beneath the slit lamp biomicroscope is integral to the prior art slit lamp assembly as no known method has been proposed to allow proper placement and translation of the slit lamp biomicroscope and its integral variable slit illumination system in the absence of a table beneath the slit lamp biomicroscope.

In the prior art, the table also supports chin rests and forehead supports to allow proper and steady positioning of the patient in relation to the slit lamp biomicroscope Although gross adjustments in the positioning of the table, height of the chin rest and height of the patient's chair and doctor's stool are necessary to accommodate individual patients, there remains the necessity of fine adjustments to the position of the slit lamp biomicroscope even after the patient has been properly positioned so that the field of view under high magnification can be focused on details on and within the eye and so that both the left and right eyes can be properly viewed without obstruction or shadows cast by the patient's nose.

The need for adjustments in the position of the slit lamp biomicroscope after the patient's head has been properly positioned has been satisfied in the prior art by allowing limited movement of the slit lamp biomicroscope in relation to the table by base by means of rolling or sliding mechanisms, using gears or cogs, and manually controlled by a joystick to move the slit lamp biomicroscope in relation to the table base.

Although the prior art is satisfactory for examining the majority of patients, a considerable and growing number cannot be satisfactorily positioned and examined due to anatomical obstructions caused by the integral table base. The table base poses a hindrance and impairs proper positioning in the case of "Restricted Individuals" such as:

i. a disabled person confined to a wheel chair or stretcher,
ii. a person with limited neck mobility or spine disorder such as kyphosis or scoliosis,
iii. an ample bosomed individual,
iv. a pregnant woman,
v. an overweight or obese person,
vi. a person of short stature or a child who has to bend forwards in an elevated examining chair and adopt a hunched posture to reach the chin rest and forehead support,
vii. a person with a stoma or wound dressing on their abdomen or chest or requiring medical devices attached to their neck or torso.

Even though the prior art slit lamp biomicroscope assemblies can be positioned close to a patient in a wheel chair rather than one seated in an exam chair, the sides of the wheelchair as well as the wheelchair's limited vertical mobility continue to present obstructions to examination.

Various attempts have been made in the prior art to overcome the difficulties of examining patients listed in the above categories with a slit lamp biomicroscope. These include modifications of the table base dimensions to reduce the space that the table occupies between the slit lamp biomicroscope and the patient. Such modifications have limited utility as they only moderately reduce the ergonomic obstacle at best, and concurrently reduce the desired mobility and stability of the supported slit lamp biomicroscope.

The only known prior art slit lamps not dependent on the previously described conventional table base assembly consist of hand held slit lamps which are small instruments supported and positioned by hand in front of the patient. The movement and positioning of such hand held slit lamps in all three spatial axes is dependent entirely on the hand and arm muscle movements of the observer holding the miniature slit lamp. Therefore, such devices cannot be accurately positioned or fixed due to normal physiological limitations Furthermore, since only one of the examiner's hands is left free proper bimanual (two handed) manipulation of the slit lamp and illumination controls is not possible.

It is important to note that examples exist in the prior art of binocular microscopes that do not require a table base and can be controllably positioned. However the present invention is to be distinguished from such prior art since it relates to a slit lamp biomicroscope, which by virtue of its variable slit illumination system serves a different function and has distinctly different components. Furthermore such prior art microscopes are not associated with chin rests or forehead supports since their utilization in opthalmology and other specialties is generally restricted to use in surgery when the patient is recumbent and immobilized.

Accordingly, it is the primary object of the present invention to provide a table-free assembly for a slit lamp biomicroscope, laser or similar ophthalmic instrument consisting of an overhead mount or canopy above the slit lamp biomicroscope which eliminates ergonomic impediment and significantly reduces anatomical barriers whilst retaining precise control of focusing, illumination and positioning, thereby allowing examination of categories of patients who cannot be properly examined using traditional prior art.

It is the further object of the present invention to provide a slit lamp biomicroscope assembly with a translation, fixation and support system located above the slit lamp biomicroscope and its integral variable slit illumination system, thereby allowing accurate and safe positioning and placement of the slit lamp (or other similar instrument) while leaving both hands of the observer free to manipulate lighting and other controls necessary to examine and treat the eyes being observed.

It is the further object of the present invention to provide a table-free slit lamp assembly located above the slit lamp biomicroscope or other similar instrument which is relatively inexpensive and easy to manufacture and more patient friendly as compared with the prior art.

Other objects and advantages of the present invention will become obvious to the reader and it is intended that these objects and advantages are within the scope of the present invention.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF SUMMARY OF THE INVENTION

This invention relates to an assembly system or mount for the placement of a slit lamp biomicroscope, laser or similar ophthalmic instrument, allowing translation or placement of the slit lamp or similar ophthalmic instrument in all three spatial axes: vertical (up and down), lateral (side to side) and anterior-posterior (forwards and back) in relation to the eyes being examined without the necessity of a table or other support below the slit lamp or similar instrument, thus reducing or preventing ergonomic obstruction and allowing accurate examination of patients (Restricted Individuals) who cannot be examined because of the aforementioned anatomical and medical restrictions listed above in the background to this invention.

The present invention provides a new and improved overhead assembly or mounting system for a slit lamp biomicroscope, variable focused illuminator, laser or any similar diagnostic or therapeutic device requiring accurate and fixed placement in relation to the human face. The present invention further provides a means for fixing the chin rests and forehead supports below the overhead mount thus preventing the need for a slit-lamp table.

The prior art slit lamp table assembly is not conducive, and causes difficulties, when using a slit lamp biomicroscope to examine the eyes of an individual in a wheel chair or anyone in the aforementioned categories of Restricted Individuals listed above. For such people the prior art slit lamp table is quite unsuitable because the rectangular nature of the prior art slit lamp table makes it difficult for an individual to get close enough to the slit lamp biomicroscope to properly rest his or her chin on the chin support and his or her forehead on the forehead support. The inability of the individual to properly rest his or her chin and forehead on the supports is likely to result in unsatisfactory testing results or the inability to properly examine or treat the individual's eyes.

The present invention allows a Restricted Individual's torso closer to the slit lamp biomicroscope thereby placing the individuals head closer to the slit lamp biomicroscope resulting in the proper placement of the patients chin and forehead on the chin and forehead supports to ensure accurate testing or treatment results.

The table-free overhead assembly or mounting system for biomicroscope, laser, or any similar diagnostic or therapeutic device requiring accurate and fixed placement in relation to the human face will accommodate a Restricted Individual by allowing proper placement of the individuals head in the chin rest and forehead support without presenting a concurrent obstruction caused by the slit lamp table normally needed for proper translation of the slit lamp biomicroscope.

There has thus been outlined, rather broadly, the more important features of the present invention in order that the detailed description thereof may be better understood, and in order that the present contribution to the art may be better appreciated. There are additional features of the invention that will be described hereinafter and that will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

LISTING OF FIGURES BY NUMBER

Figure 1:
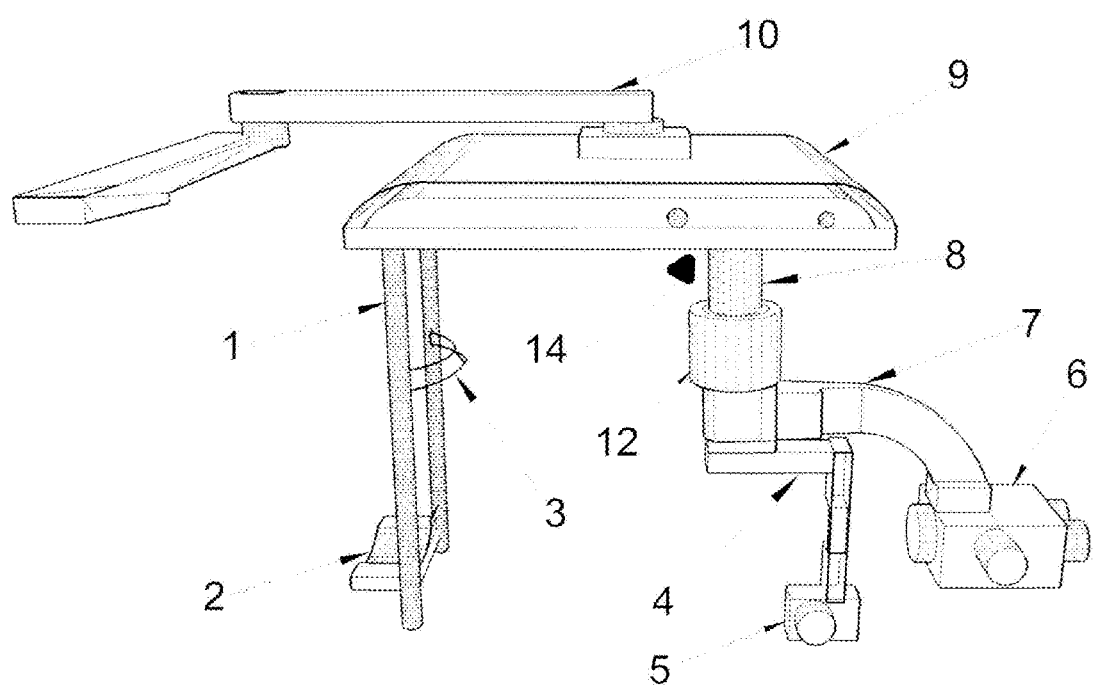
FIG. 1 is a side perspective view of the principal embodiment of the present invention with a slit lamp biomicroscope.
Figure 2:
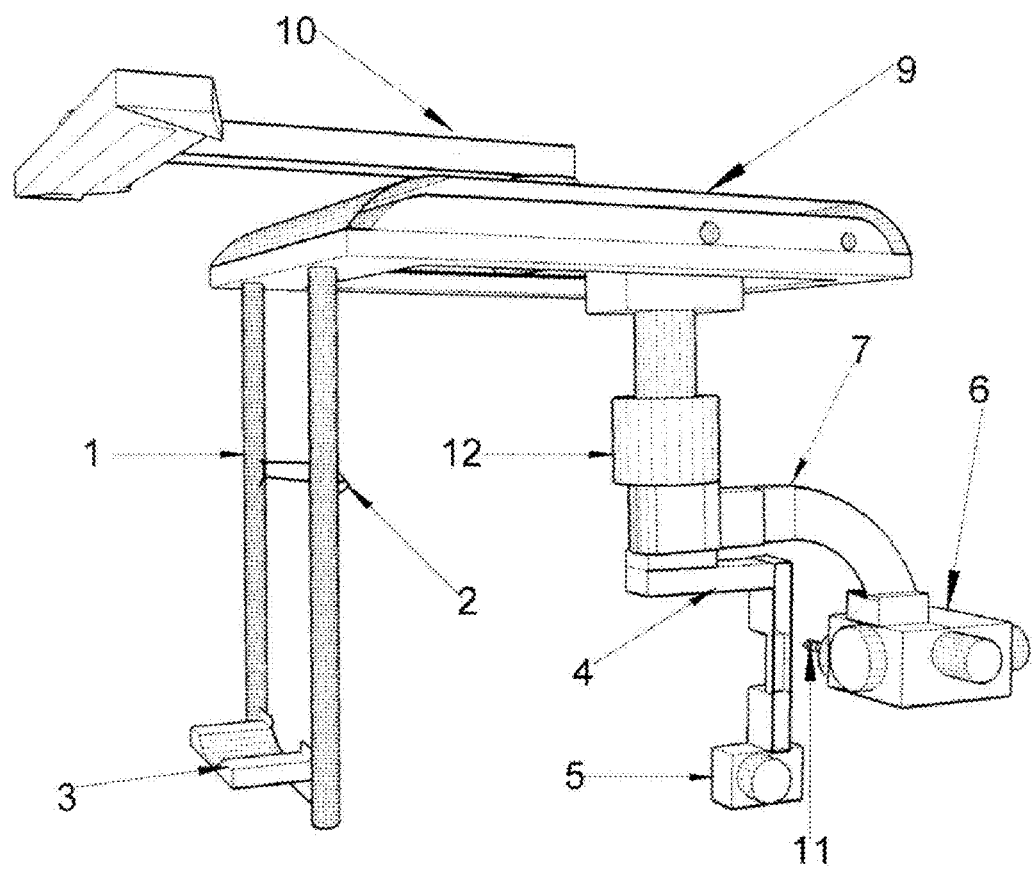
FIG. 2 is an oblique view of the principal embodiment of the present invention.
Figure 3:
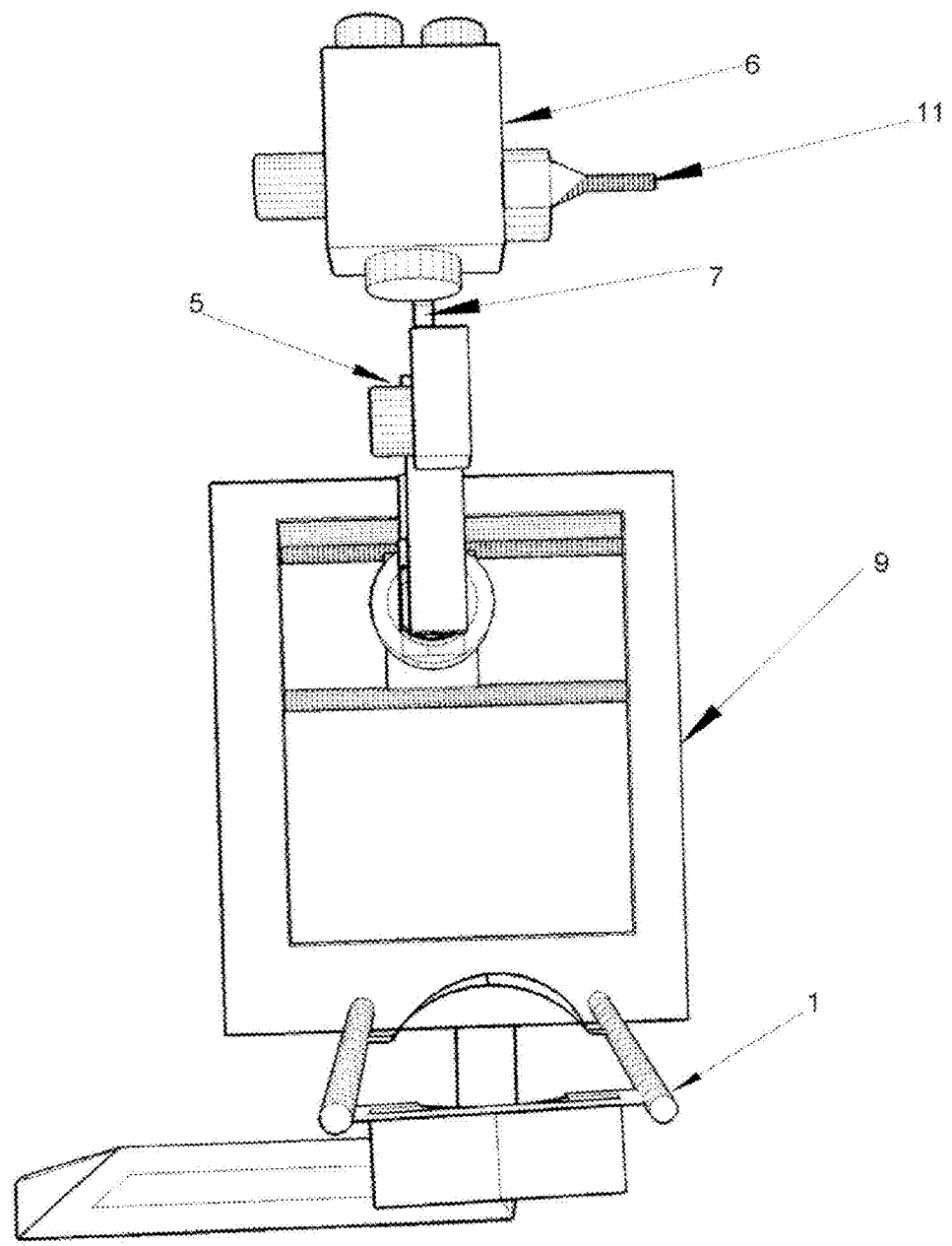
FIG. 3 is a perspective view from below of the underneath of principal embodiment of the present invention.
Figure 4:
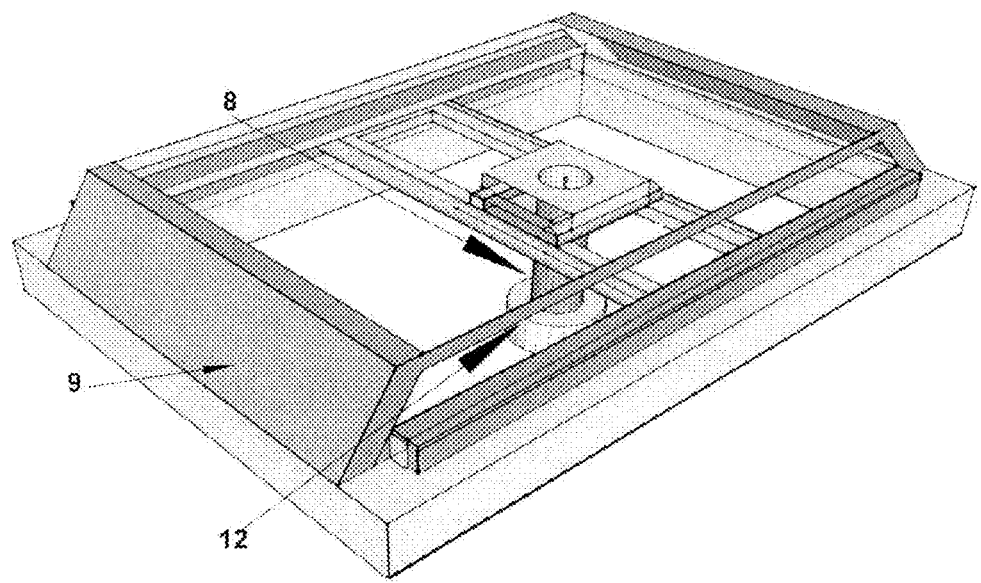
FIG. 4 is a side perspective view of the upper part of the principal embodiment of the present invention depicting a transparent outline of the arrangement allowing three dimensional translation of the slit lamp microscope.
Figure 5:
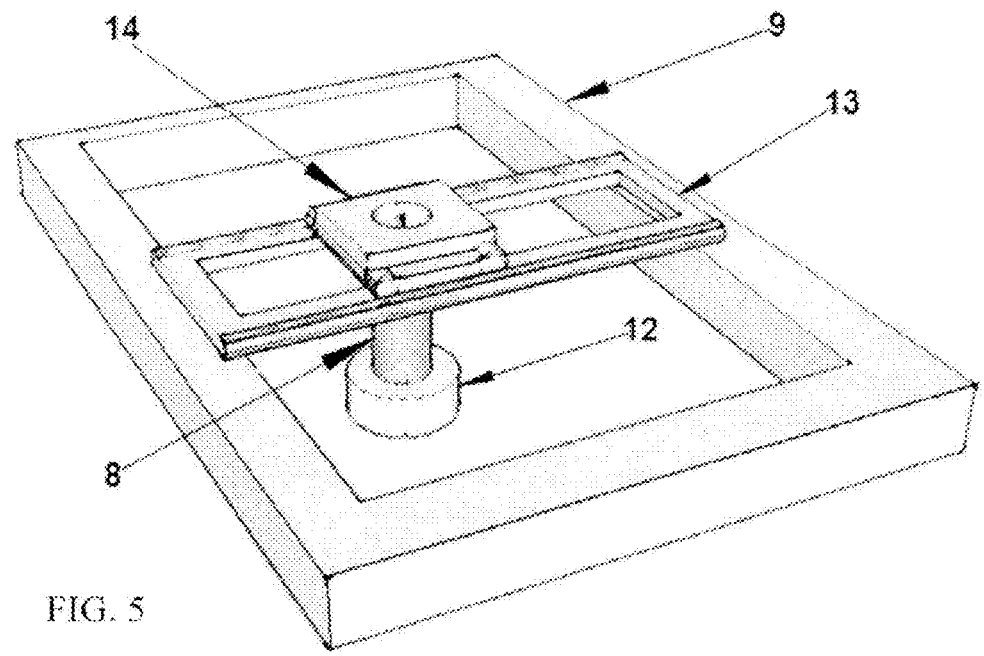
FIG. 5 is an oblique partial view of the apparatus depicted in FIG. 4 to demonstrate and clarify the relationship between the moving parts in the upper section of the principal embodiment of the present invention.

The apparatus of the invention is schematically illustrated in FIGS. 1, 2, 3, 4 and 5, in which the following numerical reference characters depict details of the invention as indicated by the corresponding lead lines:

1. A pair of vertical bars suspended from above supporting a forehead support (2) and chin rest (3).
2. Forehead support to hold patient's head steady in proper position.
3. Chin rest to support patient's head steady in proper position, whose position can be adjusted in relation to 1 to accommodate patients of varying head and neck anatomy.
4. Support arm for illumination system allowing rotation of variable slit illumination beam about a fixed vertical axis in relation to biomicroscope and patient's eye.
5. Illumination system with manual control at its lower end allowing one handed control of illumination beam parameters as well as rotation of illumination system on its support arm (4) and movement of slit lamp so that patient's eye can be examined under varying conditions of illumination.
6. Body of slit lamp biomicroscope or similar ophthalmic instrument with manual control allowing precise movement of instrument in all three spatial axes as well as rotation about a fixed vertical axis on its support arm (7).
7. Support arm for body of slit lamp biomicroscope (6)
8. Rigid vertical support column connecting hub (12) to top plate (14) allowing controlled, precise vertical translation and positional locking
9. Canopy of invention housing the translation mechanism, anchoring vertical bars (1) and connecting to overhead arm bracket (10).
10. Overhead arm bracket connects the invention to a stand, wall, table or ceiling mount so that it can be supported and moved to proper position for examining the patient and swung away to egress of the patient or storage.
11. Control handle for slit lamp or similar ophthalmic equipment.
12. Hub surrounds and overlaps with lower end of 8 and can move up and down in relation to 8.
13. Anterior-posterior frame resting within and movable forwards and backwards inside a generally rectangular canopy (9).
14. Right-left top plate suspended upon and movable laterally across the anterior-posterior frame (13) while supporting rigid vertical support column (8).

DETAILED DESCRIPTION OF THE INVENTION

Preferred Embodiment

Before explaining the disclosed embodiment of the present invention in detail it is to be understood that the invention is not limited in its application since the invention is capable of other embodiments. Also, the terminology used herein is for the purpose of description and not of limitation.

The instrument in this example is suspended from an overhead arm bracket (10) connecting the canopy of the instrument (9) to a weight-bearing stand so that the instrument may be swung in and out of position for examination of the patient and so the height of the instrument can be grossly adjusted. Because of the various options commonly available to support the bracket to the remainder of the stand or supporting structure, neither the entire stand nor the examination chair (used when the patient is not in a wheelchair or stretcher) is illustrated in the drawings as they are not central to the novel utility of the present invention. The canopy depicted in the drawings has two main functions. Firstly to support and rigidly suspend a pair or vertical bars (1) to which the forehead support (2) and chin rest (3) are attached, and secondly to provide a rigid and steady support for the anterior-posterior frame (13). In this embodiment of the invention the anterior-posterior frame slides backwards and forwards in relation to the canopy to which it is attached in a fashion allowing limited back to front movement in a horizontal plane. The anterior-posterior frame in turn supports the right-left top plate (14) allowing it limited left to right movement in a parallel horizontal plane. The controlled movements of the right-left top plate in relation to the anterior-posterior frame and the controlled movements of the anterior-posterior frame in relation to the canopy can be achieved using a number of commonly available methods such as rails, rollers, ball bearings, cogs, gears, runners or various other suitable means. In the illustrated embodiment of the present invention, rolling wheels in the form of cylindrical rods sliding over machined rails have been depicted for the purposes of clarity and simplicity.

It should be noted that the top plate could also be positioned for example, to move back to front in a horizontal plane while the frame attached to the canopy moves left to right in relation to the canopy with essentially the same result and utility as far as translation of the slit lamp biomicroscope is concerned. Therefore the relations between the top plate, frame and canopy are depicted in the preferred embodiment of the present invention in the illustrated manner because this arrangement is considered to be the most practical for construction and engineering purposes but maybe varied without altering the novelty and utility of the invention. Similarly, the drawings indicate that the right-left top plate supports the rigid vertical support column (8) and is itself supported by the anterior-posterior frame, which is in turn supported by the canopy. This appears to be the most compact arrangement allowing smooth and steady placement of the slit lamp biomicroscope, with a minimum shaking of the slit lamp biomicroscope, but may also be varied depending on the rigidity strength and weight of the material utilized for construction. Therefore, for example, the right-left top plate could be suspended from the anterior-posterior frame rather than resting above it, or the interior-posterior frame be suspended from the canopy rather than resting above it without altering the utility or novelty of the present invention.

The vertical bars (1) support a forehead support and chin rest which allow proper placement of the patient's head at the correct distance for examination using the slit lamp biomicroscope. The height of the chin rest in relation to the vertical bars can be adjusted as in the prior art by means of a rotating threaded sleeve surrounding the lower end of one vertical bar which supports a collar tube around the vertical bar. The chin rest is attached to this collar which can be moved up and down by manually rotating the threaded sleeve. For simplicity the adjusting mechanism is not illustrated in the drawing. The height of the chin rest can be adjusted to allow for normal variations in head size and specifically for variations in vertical distance between the chin and eyes of patients. In this manner the eyes of the patient may be positioned within the normal focusing range of the slit lamp biomicroscope with subsequent detailed examination being made possible by fine controlled movements of the slit lamp biomicroscope and its illumination system. An important distinction of the present invention from the prior art is that by virtue of being supported from the canopy via the vertical bars, the forehead support and chin rests allow the patient's head to be properly supported and positioned in relation to the slit lamp biomicroscope without the need for a table or any other supporting mechanism located below the patient's chin.

The rigid vertical support column (8) is perpendicular to both the anterior-posterior frame and the left-right top plate. It has is at its lower end a hub (12) which supports the slit lamp biomicroscope and its variable slit illumination system. The hub has two main functions; firstly to move up and down in a controlled fashion relative to the rigid vertical support column by means of mechanical gears, hydrostatic cylinders, electronic motors or other commonly employed practical methods, and secondly to allow rotation in a horizontal plane of both the slit lamp support arm (7) and illumination system support arm (4) about a common vertical axis. The mechanism of rotation is achieved as in conventional slit lamp arms rotating on a table mounted support, by means of tubes, collars, sleeves, washers and ball bearings.

The illumination system (5) rotates about the vertical axis which corresponds with the axis of rotation of the support arm (7) of the slit lamp biomicroscope. When the patient's head is in the correct position the vertical support arm can be controllably positioned and translated so that the patient's eye is at the correct point of focus for the current appropriate magnification of the slit lamp biomicroscope. Attention can be focused particular areas of the eye and ocular adnexa by moving the slit lamp biomicroscope backwards, forwards and sideways using the control handle (11), so that microscopic examination of the cornea, iris, lens, vitreous, retina, optic nerve etc. can be performed with at least the same level of clarity as with table-based slit lamp assemblies. The slit lamp can be rotated to obtain angular views of the eye since the point of focus remains on the axis of rotation of the slit lamp and its illumination system.

Using the control handle the slit lamp biomicroscope can be moved over to examine the fellow eye of the patient by virtue of the movements of the anterior-posterior frame and the left-right top plate in relation to each other and the canopy, without the patient having to be repositioned.

The illumination system produces a variable slit of light focused at the same point as the focal point of the slit lamp biomicroscope so that the angle of projection of the slit beam light can be altered by manually rotating the support arm for the illumination system (4). The light source is housed within the illumination system (5) and a variable light beam is projected onto the eye being examined through reflection by thin, angled mirrors to minimize obstruction of the view through the slit lamp biomicroscope (6). The shape, intensity and color of the slit beam can be manually adjusted using control knobs next to the illumination system. The position and angle of the slit beam can be manually controlled with the same hand operating the light controls by physically rotating the illumination system while grasping the light control knob. In addition, this invention will allow certain specialized maneuvers and techniques including but not limited to decentering of the slit beam, attachment of a tonometer, utilization of an additional lens to view the posterior pole of the eye etc. These have not been specifically illustrated but it should be understood that these techniques can be used with this type of slit lamp assembly just as easily as they can with table-based slit lamp assemblies except that the reduced ergonomic obstruction in the case of the present invention should facilitate such common maneuvers and techniques.

The body of the slit lamp biomicroscope (6) has the conventional controls for varying the magnification of the biomicroscope and for adjusting the eyepieces to suit the individual examiner. An important novel feature of the present invention is that control handle (11) can be used to guide and move the slit lamp biomicroscope body within the parameters in the horizontal plane set by the combination of the anterior-posterior frame, right-left top plate and canopy. By grasping the illumination system control knob in one hand and the slit lamp control handle in the other, the examiner is able to move, angle and position the slit lamp biomicroscope and it is illumination system to clearly and efficiently view both the right and left eyes under high magnification and varying conditions of illumination from the appropriate angle.

In addition to guiding forward, backward and side to side movement the control handle also adjusts the vertical height of the slit lamp biomicroscope and it is illuminating system. In the present example this is achieved by linking rotation of the control handle about its long axis by gears, pulleys or chains (not illustrated) passing through the support arm (7) and controlling vertical excursion of the hub (12) relative to the rigid vertical support column (8). There are many practical alternatives for achieving this control of vertical height such as hydrostatic cylinders or electronic motors whose details are not necessary to describe the essential function and utility of the present invention.

Furthermore, springs and counterbalance mechanisms are desirable in the present invention to minimize and distribute friction and to enhance smooth controlled movement. A variety of locking mechanisms can be employed to prevent unwanted movement when the instrument is swung in and out of position to examine the patient. For the sake of clarity springs, counterbalances and locking mechanisms have been omitted from the drawings of the preferred embodiment as have other non-essential embellishments commonly found in prior art.

Various changes and departures may be made to the invention without departing from the spirit and scope thereof. Thus it is not intended that the invention be limited to what is described in the specification and illustrated in the drawings, rather only as set forth in the claims.

Having described the invention, what is claimed as new and secured by Letters Patent is:

1. A device whereby a slit lamp biomicroscope and linked variable slit illumination system or other similar ophthalmic instrument can be suspended and controllably positioned in all three spatial axes using a combination of rollers, plates and frames located above the body of the slit lamp and not requiring a supporting table or joystick base, and wherein a table-free overhead assembly is permits controlled three dimensional movement of the slit lamp bimicroscope and variable slit illumination system, from a weight bearing canopy positioned above the patient, and in which said canopy also supports and positions the patient's head by way of a fixedly attached forehead support and chin rest, while the space beneath the suspended instrument and chin rest remains substantially free of obstructions to facilitate the examination and treatment of patients by overcoming anatomical and ergonomic obstacles commonly encountered in cases exemplified by:

1. A disabled person confined to a wheel chair or stretcher,

2. A person with limited neck mobility or spine disorder such as kyphosis or scoliosis,
3. An ample bosomed individual,
4. A pregnant woman,
5. An overweight or obese person,
6. A person of short stature or a child who has to bend forwards in an elevated examining chair and adopt a hunched posture to reach the chin rest and forehead support,
7. Or a person with a stoma or wound dressing on their abdomen or chest or requiring medical devices attached to their neck or torso.

2. The device of claim 1, wherein the means for moving a slit lamp biomicroscope or other similar ophthalmic instrument in relation to the chin and forehead support is comprised of; a generally rectangular shaped translation and support system positioned above the patient and slit lamp, allowing accurate placement, movement and fixation of the slit lamp and its illumination system in all three spatial dimensions within the desired and necessary range for examination and treatment of both eyes of a person; a system of manual controls and handles attached to the biomicroscope body and illumination system permitting bi-manual (two handed) control of the variable illumination system and the fine positioning of the slit lamp biomicroscope in all three spatial axes including vertical height by means of the control handles and associated mechanisms described herein, and eliminating the necessity of a table base or joystick control; a weight bearing arm suspending the canopy, translation mechanism, chin and forehead support, vertical column and attached slit lamp biomicroscope or similar instrument from a floor, ceiling, or wall stand.

* * * * *